US011903861B2

(12) United States Patent
Nasseri (10) Patent No.: US 11,903,861 B2
(45) Date of Patent: Feb. 20, 2024

(54) SYSTEMS AND METHODS FOR APPENDAGE SUPPORT (71) Applicant: Kennesaw State University Research And Service Foundation, Inc., Kennesaw, GA (US)

(72) Inventor: Simin Nasseri, Roswell, GA (US)

(73) Assignee: KENNESAW STATE UNIVERSITY RESEARCH AND SERVICE FOUNDATION, INC., Kennesaw, GA (US)

(*) Notice: Subject to any disclaimer, the term of this patent is extended or adjusted under 35 U.S.C. 154(b) by 443 days.

(21) Appl. No.: 17/148,891

(22) Filed: Jan. 14, 2021

(65) Prior Publication Data

US 2021/0212850 A1    Jul. 15, 2021

Related U.S. Application Data (60) Provisional application No. 62/960,984, filed on Jan. 14, 2020.

(51) Int. Cl.
*A61F 5/02* (2006.01)
*A61F 5/01* (2006.01)

(52) U.S. Cl.
CPC .............. *A61F 5/02* (2013.01); *A61F 5/019* (2013.01)

(58) Field of Classification Search
CPC .. A61F 5/02; A61F 5/019; A61F 5/026; A61F 5/028; A61F 5/0104
See application file for complete search history.

(56) References Cited

U.S. PATENT DOCUMENTS

| | | | | | |
|---|---|---|---|---|---|
| 637,156 | A | * | 11/1899 | Potts | A61F 5/028 2/44 |
| 3,750,659 | A | * | 8/1973 | Loomans | A61F 5/0104 602/23 |
| 4,813,406 | A | | 3/1989 | Ogle | |
| 5,868,691 | A | * | 2/1999 | Vishnevsky | A61F 5/026 128/845 |

(Continued)

FOREIGN PATENT DOCUMENTS

| | | |
|---|---|---|
| JP | 2018-000585 A | 1/2018 |
| WO | 2017/178847 A1 | 10/2017 |
| WO | WO-2021146385 A1 * 7/2021 | ............. A61F 5/019 |

OTHER PUBLICATIONS

Nasseri et al., "Design, Simulation and Fabrication of a New Finger Support," International Journal of Current Engineering and Technology, 8(4):954-962 (Jul./Aug. 2018).

(Continued)

*Primary Examiner* — Tarla R Patel
(74) *Attorney, Agent, or Firm* — Smith, Gambrell & Russell; Michael J. Riesen (57) ABSTRACT

Systems and methods are described for supporting an appendage or spine. In one embodiment, a support for a spine comprises a support body configured to align with a spinal column of a wearer further comprising a plurality of modular flexible support body segments configured to align with regions of the spinal column, a plurality of straps disposed along a longitudinal axis of the support body, and a support member disposed adjacent the support body to provide rigidity to the support body. The support member acts as a cantilever configured to distribute a corrective force along the length of the support body.

17 Claims, 10 Drawing Sheets

(56) References Cited

U.S. PATENT DOCUMENTS

| | | | |
|---|---|---|---|
| 5,947,915 A | | 9/1999 | Thibodo, Jr. |
| 6,719,640 B1* | | 4/2004 | Madole ............... A61F 5/026 473/215 |
| 2004/0002673 A1 | | 1/2004 | Ferraioli |
| 2006/0149180 A1 | | 7/2006 | Phelen |
| 2009/0204044 A1 | | 8/2009 | Benison |
| 2014/0228725 A1 | | 8/2014 | Summit et al. |
| 2015/0094633 A1* | | 4/2015 | Garcia ............... A61F 5/026 602/19 |
| 2017/0325988 A1* | | 11/2017 | Nadeau ............... A61F 5/026 |
| 2019/0133803 A1 | | 5/2019 | Kise et al. |
| 2020/0222222 A1 | | 7/2020 | Nasseri |
| 2021/0100674 A1* | | 4/2021 | Tzintzun, Jr. ........... A61F 5/026 |

OTHER PUBLICATIONS

Nasseri et al., "On Fabrication and Mechanical Testing of a New Finger Support," International Journal of Current Engineering and Technology, 8(4):948-953 (Jul./Aug. 2018).

Non-Final Office Action received for U.S. Appl. No. 16/742,520, dated Apr. 13, 2022, 23 pages.

Non-Final Office Action received for U.S. Appl. No. 16/742,520, dated Jun. 23, 2021, 18 pages.

Chadchavalpanichaya et al., Effectiveness of the custom-mold room temperature vulcanizing silicone toe separator on hallux valgus: A prospective randomized single-blinded controlled trial, Prosthetics and Orthotics International, vol. 42, No. 2, Apr. 2018, pp. 1-8.

Dunn et al., "Prevalence of Foot and Ankle Conditions in a Multiethnic Community Sample of Older Adults", American Journal of Epidemiology, vol. 159, No. 5, 2004, pp. 491-498.

Fraissler et al., "Treatment of hallux valgus deformity", Effort Open Rev., vol. 1, No. 8, 2016, pp. 295-302.

Holmes et al., "Correction of Intermetatarsal Angle in Hallux Valgus Using Small Suture Button Device", Foot & Ankle International, vol. 34, No. 4, 2013, pp. 543-549.

Lui et al., "Correction of Recurred Hallux Valgus Deformity by Endoscopic Distal Soft Tissue Procedure", Arthroscopy Techniques, vol. 6, No. 2, 2017, pp. e435-e440.

Martijn et al., "Fifth Metatarsal Osteotomies for Treatment of Bunionette Deformity A Meta-Analysis of Angle Correction and Clinical Condition", The Journal of Foot & Ankle Surgery, vol. 57, 2018, pp. 140-148.

Tamer et al., "Evolutionarily medicine Why do humans get bunions?", Evol Med Public Health, vol. 2017, 2017, pp. 48-49.

Willey et al., "Availability of Consumer Prices for Bunion Surgery", Foot Ankle Int., Foot Ankle Int., vol. 35, No. 12, 2014, pp. 1309-1316.

\* cited by examiner

SYSTEMS AND METHODS FOR APPENDAGE SUPPORT

CROSS-REFERENCED TO RELATED APPLICATIONS

This application is a non-provisional of and claims the benefit to Unites States Provisional Application No. 62/960,984 filed Jan. 14, 2020, which is hereby incorporated by reference in its entirety.

BACKGROUND

Many patients are suffering from back deformity, such as scoliosis, kyphosis and Scheuermann's diseases. These conditions may be painful and may cause significant trunk deformity or whole spine deformity that can progress. For example, loss of lordosis in certain regions of the lumbar or thoracolumbar spine due to kyphosis can be one of the predictors of developing chronic low back pain in adulthood. Current treatments include physical therapy, treatment of pain and bracing. With respect to bracing, treatment may lead to an improvement in kyphosis. However, current brace treatments are often accompanied by undesirable effects on the wearer, including difficulties in certain activities such as changing from a seated or lying position to a standing position. In some instances, as the time spent in a brace increases, wearers may develop low back pain. Disadvantageously, current braces or corrective apparatus are typically not usable with patients who already have distorted members and are working on them to regain some functions. Also, available supports are typically made of rough fabrics/hook and loop straps, or thermoset plastics without any flexibility. Also, most of them cannot be used for functional positions, whereas with this new support, the patients can wear them and do their normal life tasks.

Improvements are needed.

Many patients also suffer from foot deformities that can have an effect on an individual's ability to perform daily tasks. For instance, some foot deformities substantially hinder an individual's ability to walk and perform everyday functions. The most common of these deformities globally is hallux valgus (HV), commonly known as bunions. HV is defined as an abnormal angulation of the great toe deviating laterally, with the first metatarsal deviating medially. This deviation is caused by tensile forces generated in the long flexor and the extensor tendon in the foot, causing the metatarsal head to move medially. This motion causes the great toe to move in toward the second and third toes. This applies pressure to the other toes and pressure on the side of the foot which causes discomfort and pain for the individual when walking. In fact, bunions are a deformity in portions of the feet known as the hallucial phalanges and medial prominence of the first metatarsal head the deformity is often associated with the symptoms of poor balance, foot pain, and overall decreased health quality of life. Walking pattern may be a leading cause of HV, as a typical walking pattern may place an oblique shear stress and axial torsion on the Flexor Hallucis Longus and Flexor Hallucis Brevis. This oblique shear stress and axial torsion due to propulsion of the human body results in displacement of hallucial sesamoids and the intervening Flexor Hallucis Longus tendon, thus causing bunions to form. As a result, most individuals who suffer from HV have trouble walking due to the displacement of the hallux or largest toe placing pressure on the joints resulting in pain for the individual during movement.

The treatment options for HV generally fall into two categories: surgical and non-surgical. The current surgical method of fully correcting HV deformity is an intrusive surgery results in and extensive recovery and is very costly and may be out of reach for many individuals. Accordingly, more conservative non-surgical methods have been developed.

Some non-surgical approaches, which tend to be more conservative, are proper fitting footwear that have a wide and deep toe box, kinesiology tape, non-steroidal anti-inflammatory drugs, and muscle relaxants. In addition to these treatments, there exists a wide variety of orthotic options to treat HV, such as insoles, night splints, and toe separators and supports. Within the toe separator category, there are cheaper prefabricated silicon toe separators on the market, but these boast lower effectiveness when compared to surgery. The prefabricated silicon TS also have a lower compliance rate because they are not custom to the individual and thus they often do not fit the individuals foot very well and this leads to some discomfort which leads to patients being less likely to wear them.

Improvements are needed.

SUMMARY

The present disclosure relates to polymer-metal composite supports for the spine and appendages such as the foot. The support devices may be formed from a flexible, durable polymer material and may further comprise supports such as rigid supports (e.g., sheets of aluminum, steel or carbon-fiber) inserted into a soft, flexible polymer shell or casing. The supports may be fabricated to tolerate applied forces without any permanent deformation, allow for size and position adjustments, and may be used for patients who already have distorted appendages or spines and are working to regain appendage or spinal functions. The supports may provide correction of distortions while allowing a wearer to perform daily task and functions.

One embodiment of the present disclosure relates to a spine support. The spine support may comprise a modular rigid support body at least partially enclosed in a polymeric shell. The spine support may comprise a support beam attached to the support body. The support beam may be configured to encourage proper spinal alignment and posture while assisting with correction of a spinal deformity. The spine support may further comprise straps or belts configured to encircle portions of a wearer's body (e.g., head, chest, waist, etc.) and attach the support body to a wearer. The straps may be thin and flexible, and may be attached to the support body via fasteners located at various regions of the support body. Locations of the fasteners or straps, or both may be selected to provide correct alignment for the whole spine and neck. The spine support may be configured to correct spinal deformity by encouraging movement of one or more body portions (e.g., upper body and/or neck) in a direction opposite the deformity.

Another embodiment of the present disclosure relates to a support insole for an appendage. The insole is configured to prevent further deformation of a large toe and an adjacent one when worn. In some cases, bunions are often associated with flat feet. Accordingly, placing an insole into footwear that may otherwise be flat may assist in the preventing bunions from worsening. The insole provides separation of main toes via raised bunion support (e.g., a toe separator), together with cushioning that better align the toes and prevent bunions from worsening. The toe separator portion of the insole may be formed in various shapes depending on the shoes worn.

Another embodiment of the present disclosure relates to bunion support footwear. Footwear may comprise a sandal or other open-top style footwear. Footwear may include raised bunion support (e.g., a toe separator) as described with respect to support insole.

A further embodiment of the bunion support relates to a composite bandage. As with other aspects of the invention, composite bandage may comprise a thin layer of carbon fiber inserted into a flexible shell. Particularly, composite bandage comprises a flexible main body and a plurality of tabs extending perpendicularly from first and second ends of the main body and a support member disposed within at least the flexible main body to provide rigidity to the main body. Composite bandage may be configured to position the large toe. The composite bandage may be used when needed and then disposed.

The embodiments disclosed herein allow wear of the support at any stage of deformity to allow for the correction process to begin. Such embodiments also allow for simple manufacturing and changes to be made as the wearer's recovery progresses.

Methods for forming the supports described herein are also contemplated. Exemplary embodiments of the supports described herein may be fabricated using additive manufacturing (e.g., 3D printing) techniques, extrusion techniques, compression molding or like manufacturing processes.

BRIEF DESCRIPTION OF THE DRAWINGS

The following drawings show generally, by way of example, but not by way of limitation, various examples discussed in the present disclosure. In the drawings.

DETAILED DESCRIPTION

Supports for spines and appendages such as feet are shown and described.

Figure 1:
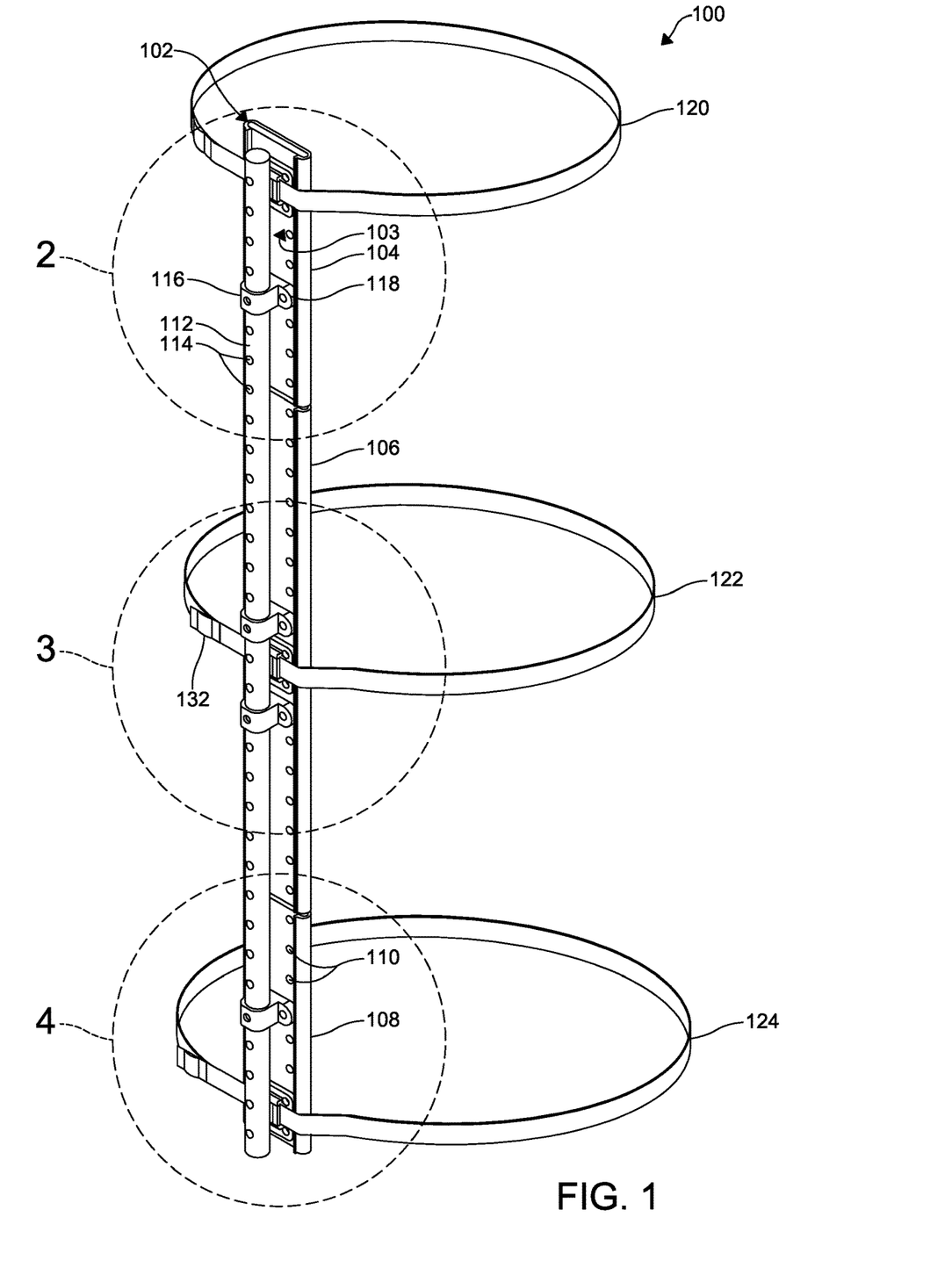
FIG. 1 shows an example spine support according to embodiments of the disclosure.
Figure 2:
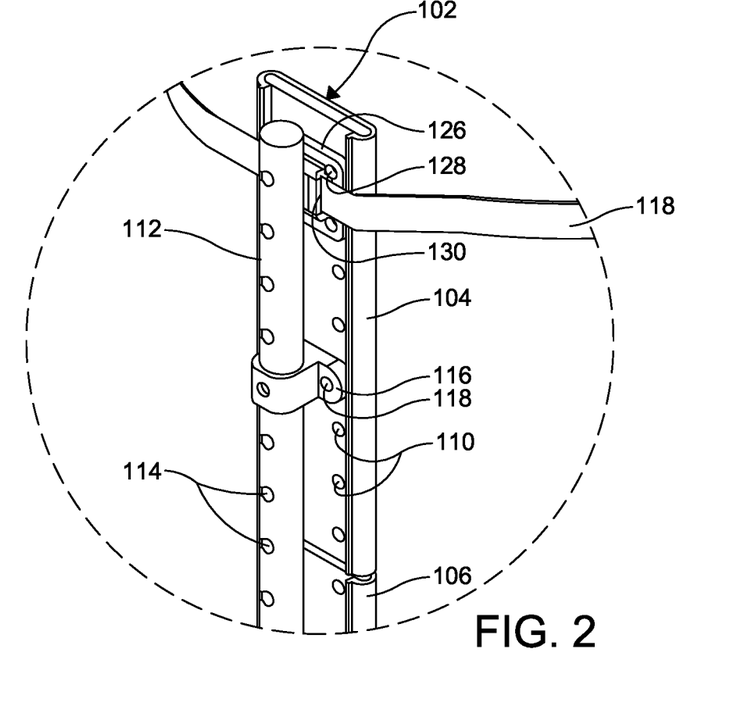
FIG. 2 shows a detail view of an example spine support according to embodiments of the disclosure.
Figure 3:
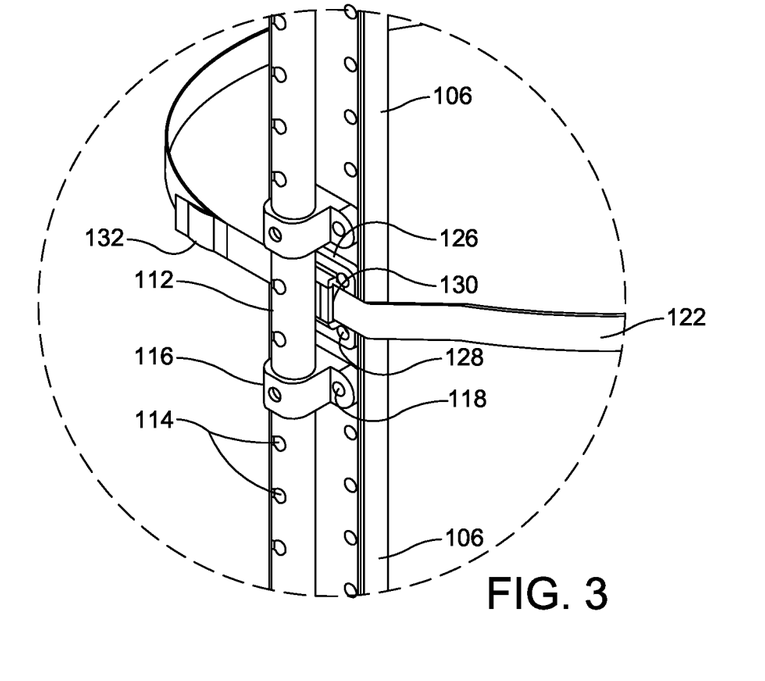
FIG. 3 shows a detail view of example spine support according to embodiments of the disclosure.
Figure 4:
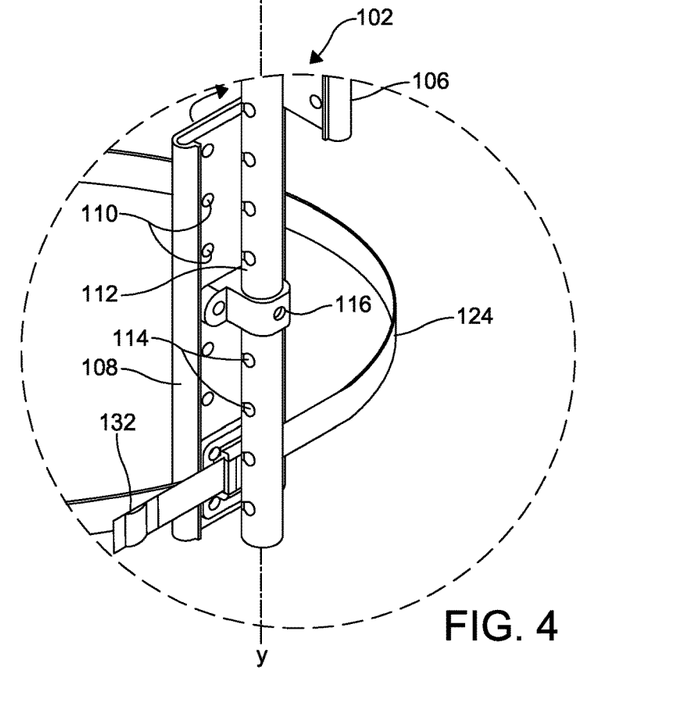
FIG. 4 shows a front view of example spine support according to embodiments of the disclosure.
Figure 5:
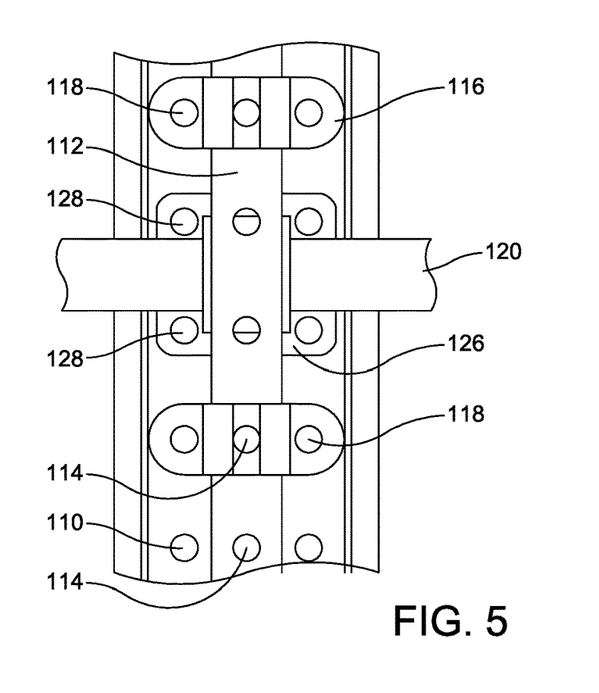
FIG. 5 shows a detail view of example spine support according to embodiments of the disclosure.

As an illustrative example, a spine support is disclosed. FIG. 1 shows an example spine support 100 according to embodiments of the disclosure. FIG. 2 shows a detail isometric view of an example spine support 100 according to embodiments of the disclosure. FIG. 3 shows a detail isometric view of example spine support 100 according to embodiments of the disclosure. FIG. 4 shows a front view of example spine support 100 according to embodiments of the disclosure. FIG. 5 shows a detail isometric view of example spine support 100 according to embodiments of the disclosure.

The spine support 100 may be formed as modular rigid support body 102 including a plurality of segments. In some embodiments, the support body 102 may comprise three segments (e.g., segments 104, 106, 108). The spine support 100 is configured to align with a spinal column of a wearer such that, when worn, the support 100 may provide deformation correction. The support body 102 is configured to be height adjustable. In some embodiments, the support body 102 may contract or expand via a telescoping mechanism configured to provide a customized fit for a wearer. The support body 102 may be modular, such that individual segments 104, 106, 108 may be added or removed to accommodate a wearer's spine. Spine support 100 may be configured to be "one-size-fits-all". Specifically, the support body 102 may be configured to increase or decrease in length as needed. As used herein, spinal (or vertebral) column may refer to a flexible column extending from neck to tail, comprised of a series of bones (the vertebrae) as is known in the art. The support 100 and/or any of its respective components are generally configured to encourage proper alignment of the spinal column, such that it encourages a body to maintain a relatively straight line from the head down along a centerline through the shoulders and back. Such alignment, as well as the causes and result of spinal misalignment, are generally known in the art.

For instance, the spine support 100 may start in a first configuration suitable for a first height range, up to a maximum height. For heights greater than the first height range, one or more of the segments 104, 106, 108 may be extended to accommodate a greater height range (e.g., taller people). In such a way, a plurality of lengths can be selected for the support body 102 to accommodate variations in height. The support body 102 may include a plurality of segment apertures 110 configured to receive fastening means (e.g., bolts, screws, etc.) used for affixing support components to one or more support body segments 104, 106, 108 adjusting the support components to accommodate various wearer sizes.

The spine support 100 may further comprise a support member or beam 112 attached to a first flat side 103 of the support body 102 along a longitudinal axis y of the support body 102. When worn, the support body 102 may be disposed between the wearer and the support beam 112 when the support 100 is coupled to the wearer. In some aspects, support beam 112 may be a cylindrical support beam 112 or rod. The spine support 100 components may be manufactured in a plurality of sizes, to account for variations in patient height. In such configurations, the support beam 112 may be selected based on the dimensions of the body (e.g., based on the sum of lengths of the segments 104, 106, 108). Accordingly, the support beam 112 may include a plurality of support beam apertures 114 configured to receive fastening means (e.g., bolts, screws, etc.) used for affixing support components to the body and adjusting the support components to accommodate various wearer sizes. The spine support 100 may further comprise one or more support beam fasteners 116 further comprising one or more support beam fastener apertures 118 for attaching the support beam 112 to the support body 102.

When worn, the force of a spinal deformity may be applied to the support beam 112 that is inserted into the support body 102. The support beam 112 acts as a cantilever beam and correct equilibrium equations can be applied to the support beam 112. A force may be applied by the spine support 100 where the support body 102 of the spine support 100 contacts the spine. The deformity may cause the spine to put force on the rigid support body 102, resulting in a cantilever beam with distributed forces acting along the length of the support body 102 and spine.

Figure 14:
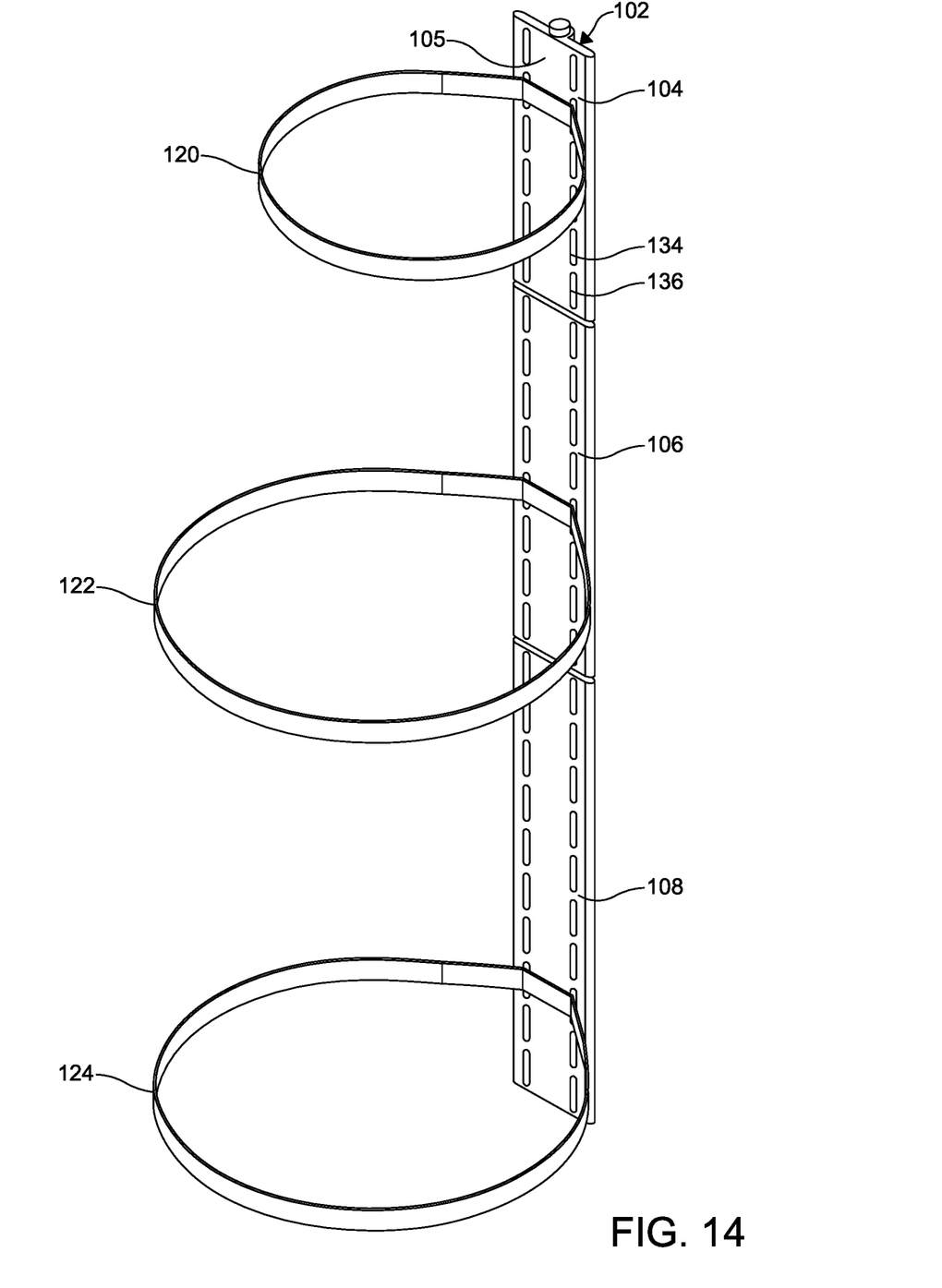
FIG. 14 shows an example spine support with embedded support beam according to embodiments of the disclosure.
Figure 15:
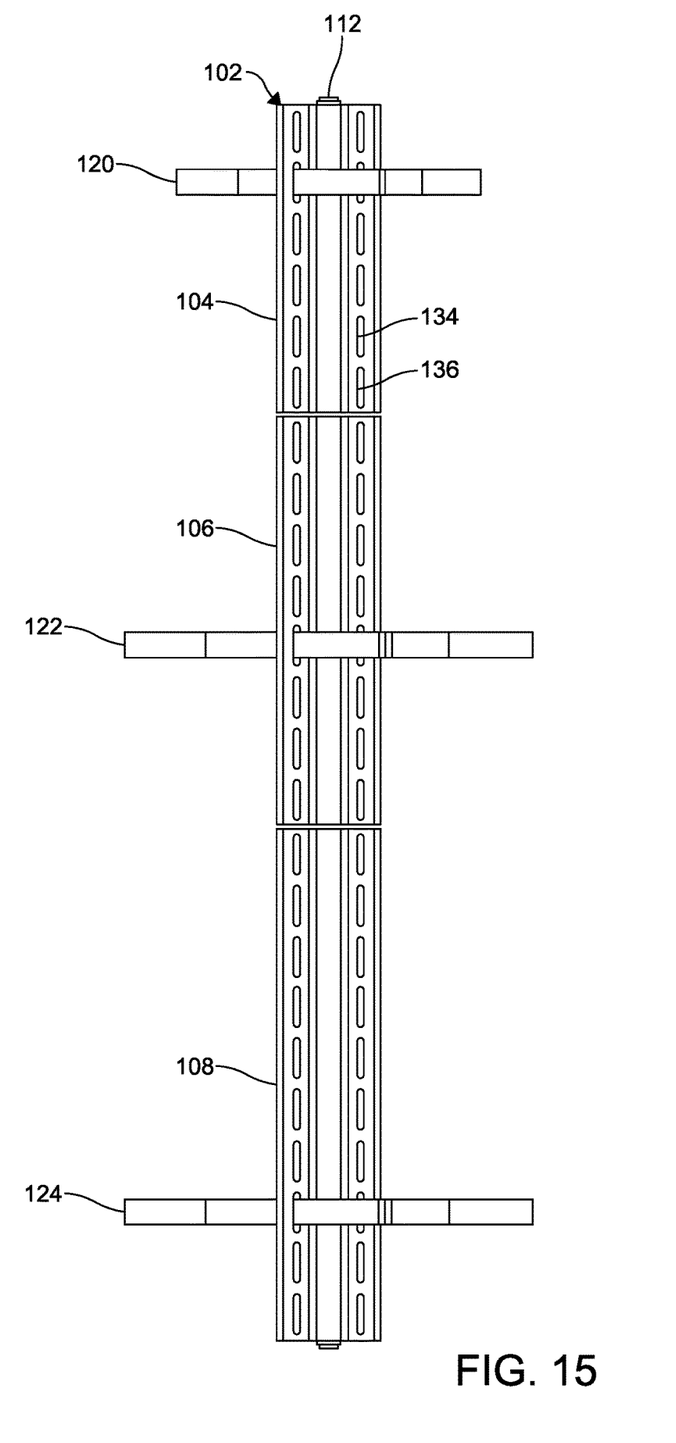
FIG. 15 shows a rear view of an example spine support with embedded support beam according to embodiments of the disclosure.
Figure 16:
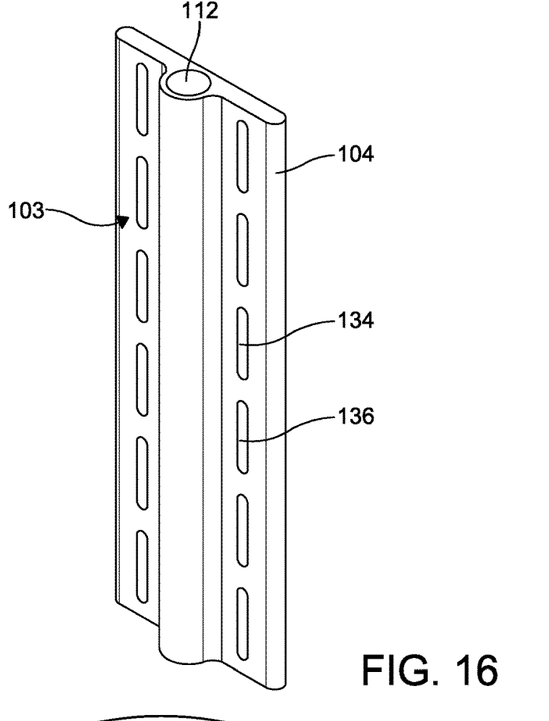
FIG. 16 shows a detailed isometric view of an example spine support with embedded support beam according to embodiments of the disclosure.
Figure 17:
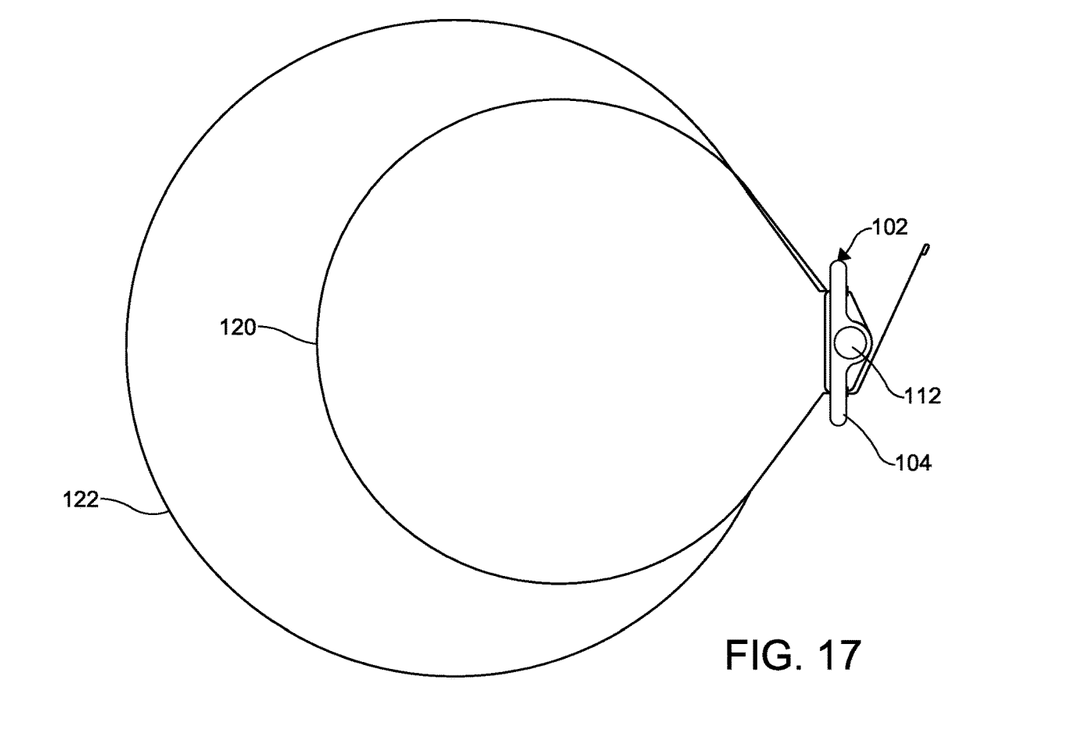
FIG. 17 shows a top view of an example spine support with embedded support beam according to embodiments of the disclosure.

In some embodiments, portions of the support beam 112 may be hollow to reduce the overall weight of the spine support 100. In some embodiments, for instance to minimize the overall thickness of the spine support 100, the cylindrical support beam 112 may be embedded within or inserted into the support body 102. FIG. 14 shows an example spine support with embedded support beam according to embodiments of the disclosure. FIG. 15 shows a rear view of an example spine support with embedded support beam according to embodiments of the disclosure. FIG. 16 shows a detailed isometric view of an example spine support with embedded support beam according to embodiments of the disclosure. FIG. 17 shows a top view of an example spine support with embedded support beam according to embodiments of the disclosure. As can be seen, the support beam 112 may be inserted into or through any of segments 104, 106, 108 along a vertical or longitudinal axis y. Such configurations may be desirable to minimize the overall profile of the spine support 100.

The modular and/or telescopic design of the spine support 100 facilitates changes in length as well as isolated rotation of any of one or more the segments 104, 106, 108 independent of one or more of the remaining segments. The spine support 100 may be configured to provide rotation about the vertical or longitudinal axis y which passes through the support body 102. The spine support 100 may be modular to provide isolated/supported rotation for portions of the spine as needed. Specifically, the segments 104, 106, 108 are configured to move independently of one another. In some instances, segments 104, 106, 108 are configured to rotate about the longitudinal axis y of the support body, such that, for instance, when a wearer rotates a body portion (e.g., neck, upper back, waist, etc.), the segment supporting the rotating body portion also rotates. Thus, for the comfort of the wearer, a first segment (e.g., a neck segment) is configured to rotate (and therefor provide supported rotation of the neck) independent of any other segments 104, 106, 108 (e.g., upper back, mid-back, waist, etc.), as can be seen in FIG. 4. A second segment (e.g., an upper/mid-back segment) is configured to rotate (and therefor provide supported rotation of the upper back/chest) independent of any other segments 104, 106, 108 (e.g., neck, waist, lower back etc.). A third segment (e.g., a lower back segment) is configured to rotate (and therefor provide supported rotation of the mid-back/waist) independent of any other segments 104, 106, 108 (e.g., neck, upper back, mid-back etc.).

The spine support 100 may further comprise a soft, flexible outer layer. In some embodiments, flexible outer layer may be a sleeve (e.g., a polymeric sleeve) into which support body 102 may be inserted. Sleeve provides a soft contact area for the body of a wearer. In some embodiments, flexible outer layer may be a coating applied over one or more segments 104, 106, 108 and/or support beam 112 or any components thereof.

The spine support 100 may comprise a plurality of straps 120, 122, 124 (e.g., wraps or belts) configured to encompass a section of a wearer's body. Straps 120, 122, 124 may be flexible. The straps may be disposed along a longitudinal axis y of the support body 102 The straps 120, 122, 124 may be moveable such that they can be relocated by the aid of this modular system as well, accommodate a plurality of body configurations. The straps 120, 122, 124 are configured to encircle a wearer's body at various locations along with a rigid shaft that provides the needed stiffness to correct the joint deformity. In one embodiment, straps 120, 122, 124 may be configured to encircle the head, a trunk region generally located under the chest and the waist of a wearer. These locations are selected to provide correct alignment for the whole spine and neck. This arrangement helps to correct the deformity by pulling the upper body and neck in the opposite direction of the deformity.

The straps 120, 122, 124 are configured to be modified easily. For instance, both the diameters of the straps 120, 122, 124 and also the distance between them can be adjusted via the modular support body 102. One or more strap fasteners 126 may be attached to one or more of support body segments 104, 106, 108. To this end, strap fasteners 126 may include one or more apertures 128 configured to attached strap fastener 126 to a support body segment. The strap fasteners 126 may also include openings or slots 130 configured to receive one or more strap portions to releasably affix a strap to a portion of the elongate support body 102. The straps 120, 122, 124 may include one or more securing ends 132. To affix a strap to the elongate support body 102, a strap 120, 122, 124 may be inserted through a slot 130 and adjusted to a desired circumference. The strap may then be fastened to the support body 102 in the desired location using the strap fastener 126. Specifically, a fastening device may be inserted through one or more support beam apertures 114 aligned with the strap fastener 126 and contact the strap to hold the strap in place. In such embodiments, the securing device is not inserted through the strap.

As can be further seen, in this or other embodiments, the support body apertures may be elongate apertures 134, 136. In such configurations, one or more of the plurality of straps 120, 122, 124 may be configured to be inserted through the elongate apertures 134, 136. One or more of the plurality of straps 120, 122, 124 may be configured to contact a second flat side 105 of the support body 102. In this manner, one or more of the plurality of straps 120, 122, 124 may be configured to double back over itself to provide a frictional hold (or additional hold) of the strap in place.

The dimensions of the straps 120, 122, 124 are configured to be modified easily. For instance, the diameters of the straps 120, 122, 124 and the distance between them can be adjusted via the modular rigid support body 102. To this end, the support body 102 comprises a plurality of apertures configured to receive the straps 120, 122, 124 so that the straps 120, 122, 124 may be secured at desired locations along the support body 102. In alternative embodiments, a plurality of slots or openings may be formed along the support body through which the straps 120, 122, 124 may be inserted, as can be seen in FIGS. 14-17.

In other embodiments, the securing end 132 may include one or more "one-way" tabs or protrusions. In such an embodiment, after the strap has been inserted through the slot and adjusted to a desired circumference, the one-way tab may prevent the strap from increasing in circumference. To remove the strap, strap may be depressed to allow the one-way tab to slide through the slot. The slot may be configured to be flexible, permitting removal of the tabbed strap when the strap is depressed.

The straps 120, 122, 124 may be height adjustable and used both to accommodate variations in the height of wearers and accommodate and isolate a deformity in one region of the body (e.g., the lower spine, upper spine, neck, etc.) In such instances, one or more straps 120, 122, 124 (e.g., the upper strap for lower back deformity) may be removed. Other configurations may be used for other targeted areas of deformity.

The spine support 100 may be durable and rigid enough to withstand daily. Spine support 100 may also allow for size and position adjustments, and can be used for patients who already have distorted members and are working on them to regain some functions. Spine support 100 may be used in various functional positions, allowing a wearer to perform normal life tasks while benefiting from wearing the support.

The spine support 100 is configured to be flexible and comfortable enough to be worn daily and provide correction over a period of time without the need for surgery. The spine support 100 is configured to be worn with clothing and allows for daily use. The spine support 100 may be configured to correct the deformity by pulling the upper body and neck in the opposite direction of the deformity. The spine support 100 may be constructed using a combination of a polymer material and metal or carbon fiber inserts to provide corrective support. Namely, the flexible components of the spine support 100 may be constructed of a polymer based material and the rigid support member (e.g., solid support beam 112) used to correct the deformity may be formed from a rigid material such as a metal or carbon fiber. The spine support 100 may be low profile and designed for maximum mobility and correction for the wearer.

Methods for forming one or more supports such as the spine support 100 may include one or more first fabrication processes. Fabrication processes for creating a support such as the spine support 100 may include extrusion, additive manufacturing (or 3D printing), and compression molding. For instance, the spine support 100 may be fabricated using a 3D PolyJet printer. Additive manufacturing or 3D printing allows for a fully supported print, enabling printing of flexible spine support components. The materials used to form the spine support 100 may be selected based on desired material properties such as weight and elastic modulus. Elastomers (e.g., natural rubber, synthetic rubber, and thermoplastic elastomers) that provide sufficient elasticity and extensibility may be utilized or forming at least a portion of the flexible wraps or spine support 100 sheath and/or other flexible components of the spine support 100. Advantageously, elastomers used to form the spine support 100 flexible components may be soft to the touch and reduce or minimize skin irritation for a wearer, and provide a comfortable fit around the body that is resistant to tearing. In exemplary embodiments, a tear resistant polymer, such as DuraForm® Flex is utilized. Other materials may be used, including, but not limited to, TangoBlack, TangoGray, or Agilus 30 FLX, and other DuraForm® polymers. Agilus30-FLX has high tensile tear resistance (5-7 kg-cm$^1$). The Agilus30 family of polymers provides superior tear-resistance, elongation at break and rubber-like texture. In some embodiments, a fiber reinforced polymer (FRP) material may be used. A support resin (e.g., Fullcure 705) may be utilized during the printing process. In some aspects, the support body 102 may be constructed using a 3D printed polymer such as a thermoplastic elastomer (TPU or TPE) which is soft, extensible and tear resistant. In some embodiments, the spine support 100 devices described herein may be a composite devices composed with metal or carbon fibers mixed with a polymer material, which may impart greater strength onto the spine support 100. For instance, a Connex 3D printer capable of printing with multi-material may be utilized to form composite spine support 100 components.

The use of a spine support 100 for correction will allow the wearer to wear the device daily and provides a noninvasive method to correct the deformity. The spine support 100 allows the patient to go about daily activities while wearing the brace and still be fully mobile. The design and materials used to form the spine support 100 may be selected with patient mobility as a priority. The polymer material that surrounds the rectangular pieces 104, 016 and 108 allows for a comfortable fit that can be worn for extended periods of time. The spine support 100 may correct the deformity by applying a slight pressure in the opposite direction of the curvature resulting in the gradual straightening of the spine. The soft polymer is configured for wearer comfort, while the rigid support body 102 provides sufficient rigidity to correct the deformity. The combination of these components provides effective correction of the deformities, with patient use and comfort as a priority.

Figure 6:
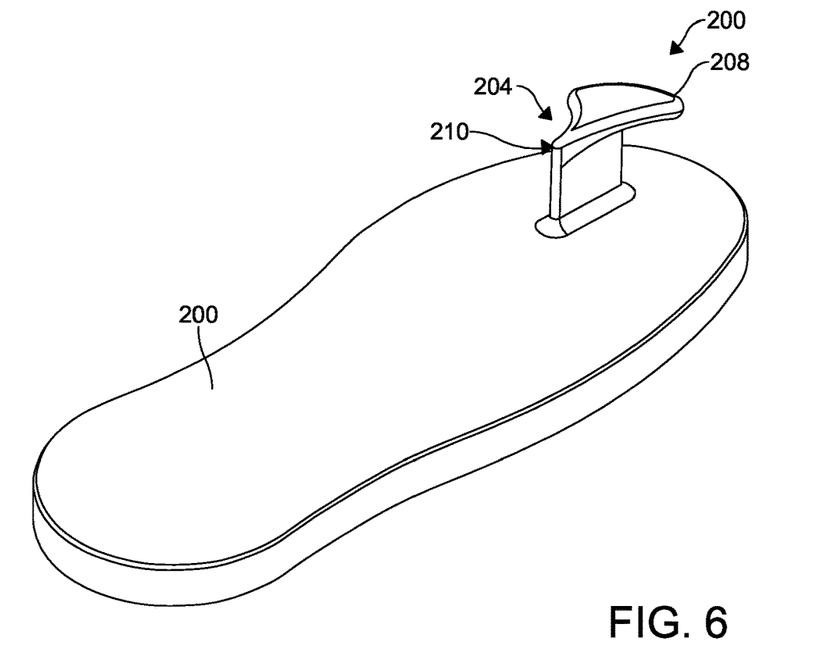
FIG. 6 shows an isometric view of a composite shoe insole according to embodiments of the disclosure.

In another aspect of the disclosure, a support insole 200 is disclosed. FIG. 6 shows a composite support insole 200 according to embodiments of the disclosure. The support insole 200 is configured to correct hallux valgus foot deformity, more commonly known as a bunion. Namely, the support insole 200 is configured to prevent further deformation of the large toe and the adjacent one. In some cases, bunions are often associated with flat feet, placing insoles into shoes that are otherwise flat can help prevent bunions from worsening. The support insole 200 is configured to allow the support to be worn within a shoe and allows for daily use. The insert provides a location for a reaction force opposing the bunion. This reaction helps to correct the deformity by pulling the toes in the opposite direction of the deformity. The support insole 200 may be constructed using a combination of a polymer material and metal or carbon fiber inserts to provide corrective support. Namely, the flexible components of the support insole 200 may be constructed of a polymer based material and the rigid support member (e.g., solid support beam) used to correct the deformity may be formed from a rigid material such as a metal or carbon fiber. The support may be low profile and designed for maximum mobility and correction for the wearer.

The support insole 200 is configured to provide separation of the first and second toes, together with cushioning that in combination better align the toes to assist in the prevention of an increase in bunion size or severity. The support insole 200 is designed to be flexible enough to be worn daily and provide correction over a period of time without the need for surgery. The support insole 200 components may have certain material properties that allow support insole 200 to be worn by the patient with minimal irritation. The support insole 200 is configured to straighten a bent toe overtime, while providing comfort and functionality. The support insole may also reduce inflammation and relieve pain during moments of discomfort.

The support insole 200 may comprise a base 202 and a raised bunion support 204 (e.g., a toe separator). The raised bunion support 204 may be positioned on the base 202 such that when the insole is inserted into an article of footwear (or formed into an article of footwear), the bunion support 204 is positioned between first and second toes of a wearer. The bunion support 204 may include a base 202 such formed generally as an insole or sole of an article of footwear. The base 202 may include a toe portion, a heel portion and a region therebetween. The base 202 of the support insole 200 may comprise a metal sheet inserted into flexible polymer material. In some aspects, sheet materials such as aluminum 6061-T6 (SS) or carbon fiber may be utilized. The base 202 may be formed in a variety of shapes to conform to the type of shoe with which the support insole 200 may be used.

The bunion support 204 portion of the support insole 200 may include a thin flat side support 206 portion positioned orthogonally to the base 202 and affixed to the base 202, and a flat wide top support portion 208. The top support portion 208 is generally parallel to the base 202 (and perpendicular to the side support portion 206). In some embodiments, the top support portion 208 may be substantially tear drop shaped to conform to the curvature of a toe box. As discussed, the support insole 200 may prevent further deformation of the large toe and the adjacent one. In some cases, bunions are often associated with flat feet, placing insoles into shoes that are otherwise flat can help prevent bunions from worsening. Also, the flat wide top support portion 208 of the bunion support 204 is configured to push the second toe (e.g., the pointer or index toe) in a generally downward direction. Such downward force may correct a pointer toe deformity (e.g., hammer toe) caused by deformation of the big toe. Thus, the top support portion 208 of the bunion support 204 is configured to reduce or prevent further the deformations of the toes.

The apex 210 of the top support portion 208 may point toward the heel portion of the base 202. As shown in FIG. 6, the top support portion 208 is pointing toward the back of the insole. In some embodiments, top support portion 208 points toward the front of the base 202, depending on the particular toe deformity. The top support portion 208 may also be round or rectangular. The side support portion 206 (i.e., the portion that would be positioned between the first and second toes) may gradually decrease from a first height 212 at a first end to a second height 214 at a second end. The second height 214 may be less than the first height 212. In preferred embodiments, second end may be the end closest to the circumferential edge of the toe portion of the base 202. To this end, the support insole 200 may be configured to be inserted into a shoe comprising a tapered toe box.

The support insole 200 provides longitudinal and transverse arches for the foot. To this end, one or more raised curvatures may be formed in the base 202. When worn, the raised curvatures may provide sufficient upward pressure on the foot such that the body weight of a wearer is evenly distributed. Specifically, the raised curvatures may prevent uneven distribution of pressure in certain regions of the foot (e.g., it may prevent too much pressure on the ball of the foot), therefore relieving forefoot. By its configuration, the support insole 200 may reduce fatigue and discomfort to the feet, hips, legs, and knees. By its configuration, the bunion insole may improve balance reactions, increase blood circulation, and reduce muscle strain.

Methods for forming one or more support insoles such as the support insole 200 may include one or more first fabrication processes. Fabrication processes for creating support insole 200 may include extrusion, additive manufacturing (or 3D printing), and compression molding. For instance, the support insole 200 may be fabricated using a 3D PolyJet printer. Additive manufacturing or 3D printing allows for a fully supported print, enabling printing of flexible support insole components. The materials used to form the support insole 200 may be selected based on desired material properties such as weight and elastic modulus. Elastomers (e.g., natural rubber, synthetic rubber, and thermoplastic elastomers) that provide sufficient elasticity and extensibility may be utilized or forming at least a portion of the flexible straps or support insole sheath and/or other flexible components of the support insole 200. Advantageously, elastomers used to form support insole flexible components may be soft to the touch and reduce or minimize skin irritation for a wearer, and provide a comfortable fit around the body that is resistant to tearing. In exemplary embodiments, a soft, flexible and tear resistant polymer, such as DuraForm® Flex is utilized. Other materials may be used, including, but not limited to, TangoBlack, TangoGray, or Agilus 30 FLX, and other DuraForm® polymers. Agilus30-FLX has high tensile tear resistance (5-7 kg-cm$^{-1}$). The Agilus30 family of polymers provides superior tear-resistance, elongation at break and rubber-like texture. In some embodiments, a fiber reinforced polymer (FRP) material may be used. A support resin (e.g., Fullcure 705) may be utilized during the printing process. In some aspects, the support body may be constructed using a 3D printed polymer such as a thermoplastic elastomer (TPU or TPE) which is soft, extensible and tear resistant. In some embodiments, support insole devices described herein may be a composite devices composed with metal or carbon fibers mixed with a polymer material, which may impart greater strength onto the support insole 200. For instance, a Connex 3D printer capable of printing with multi-material may be utilized to form composite support insole components.

The use of the support insole 200 for correction will allow the wearer to wear the device daily and provides a noninvasive method to correct the deformity. Support insole 200 allows the patient to go about daily activities while wearing the brace and still be fully mobile. The design and materials used to form the support insole 200 may be selected with patient mobility as a priority. The polymer material that surrounds the toes allows for a comfortable fit that can be worn for extended periods of time. The support insole 200 corrects the deformity by applying a slight pressure in the opposite direction of the curvature resulting in the gradual straightening of the joint. The use of the rigid support member (e.g., rigid support beam or insert) allows the soft polymer to be used for comfort and the rigid support member provides the rigidity needed to correct the deformity. The combination of these components provides effective correction of the deformities with patient use and comfort as a priority.

The force of the toe deformity is applied to the bunion support 204. In some instances, a hallux valgus deformity may have an angle ranging from 15 to 45 degrees. The deformity may cause the toes to put forces on the bunion support 204, resulting in a cantilever beam with distributed forces acting along the length of the bunion support 204 and toe.

The support insole 200 dimensions may be small to allow the patient to wear the support inside footwear of their choice. The support insole 200 may be inserted into, for instance, a shoe or boot. Alternatively, the insole may be formed into an article of footwear. In some embodiments, the article of footwear comprises a sandal. While the bunion support 204 sandals are known in the art, such sandals tent to exert a large amount of pressure on a bunion itself, as the bunion may rub against a component of the sandal (e.g., an internal wall of a top or toe portion of the sandal).

Figure 7:
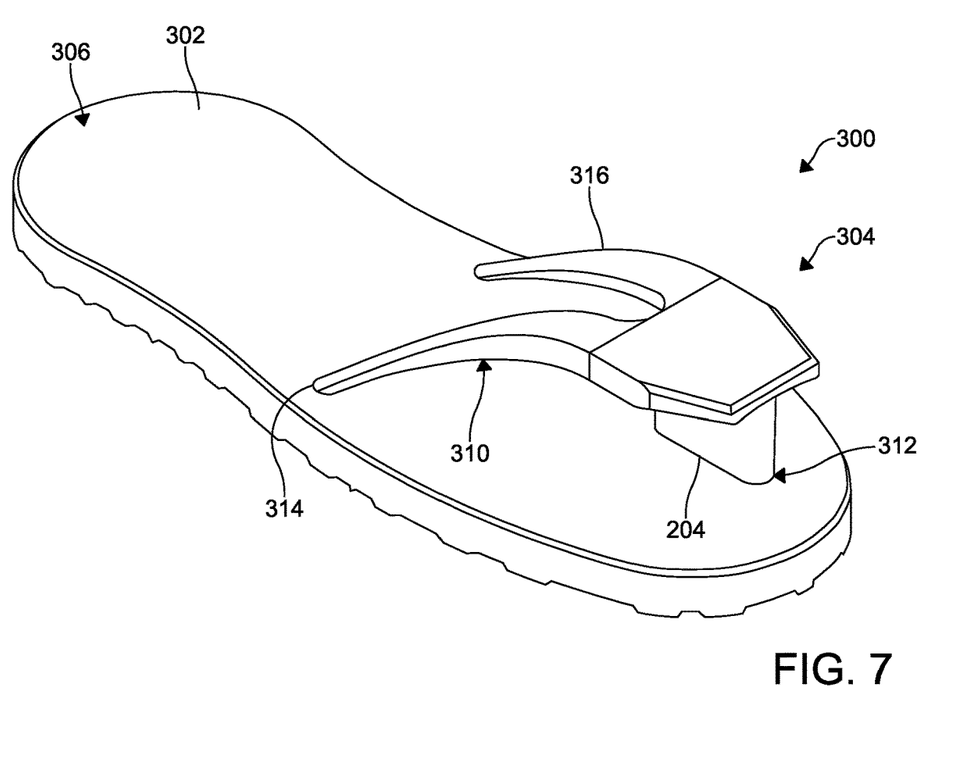
FIG. 7 shows an isometric view of an example bunion support footwear article according to embodiments of the disclosure.
Figure 8:
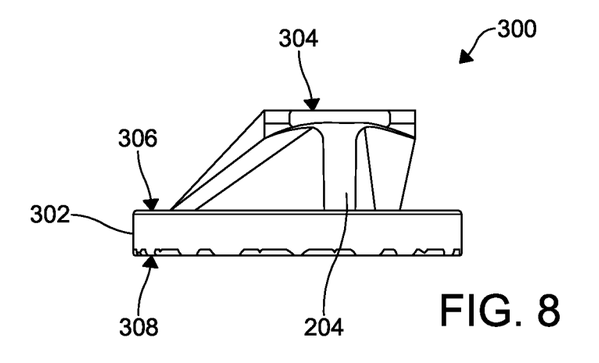
FIG. 8 shows a side view of example bunion support footwear article according to embodiments of the disclosure.
Figure 9:
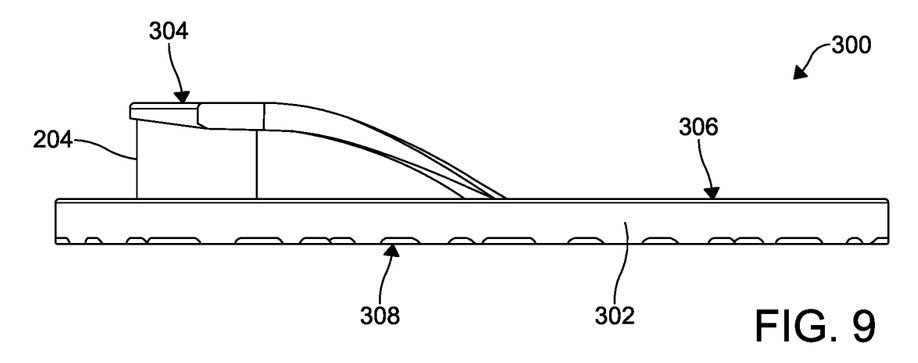
FIG. 9 shows a side view of example bunion support footwear article according to embodiments of the disclosure.
Figure 10:
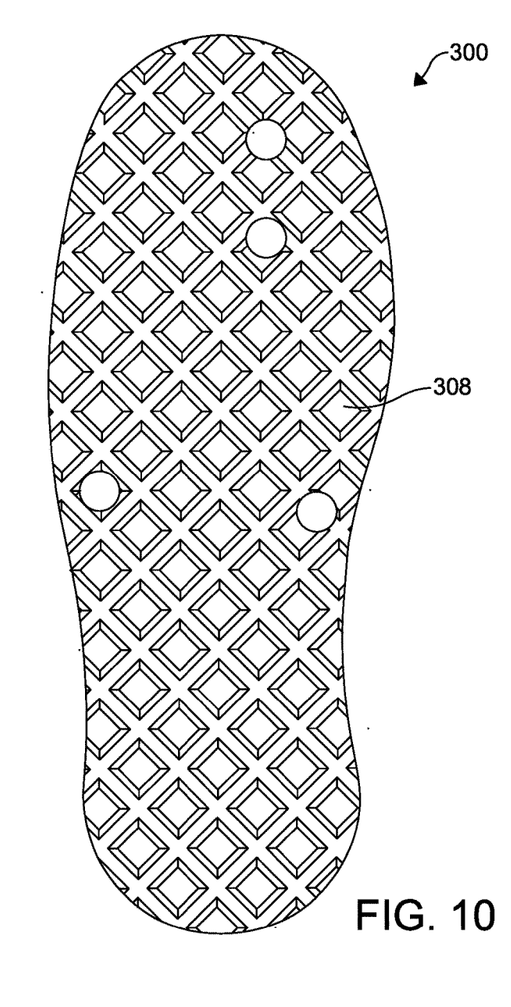
FIG. 10 shows a bottom view of example bunion support footwear article according to embodiments of the disclosure.
Figure 11:
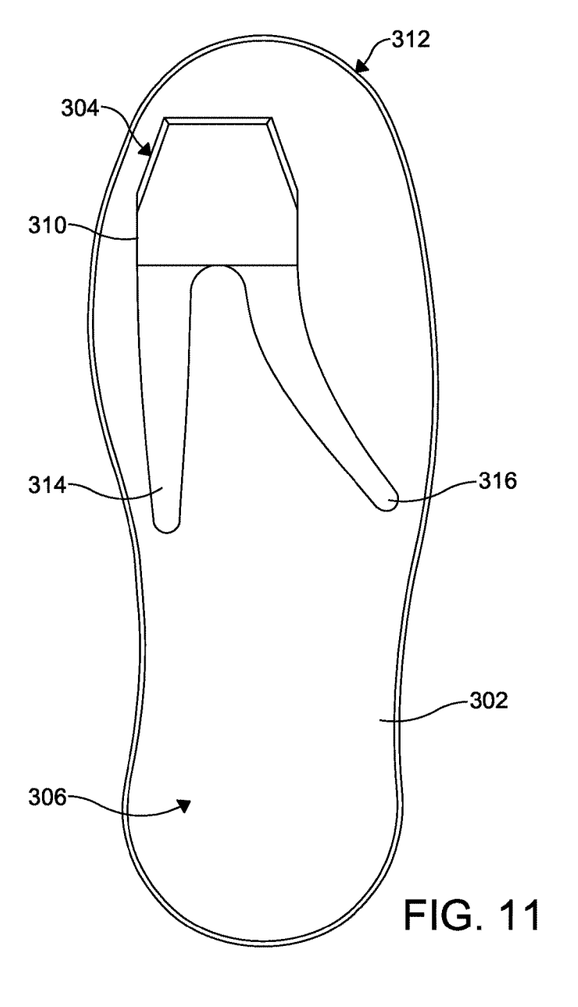
FIG. 11 shows a top view of example bunion support footwear article according to embodiments of the disclosure.
Figure 12:
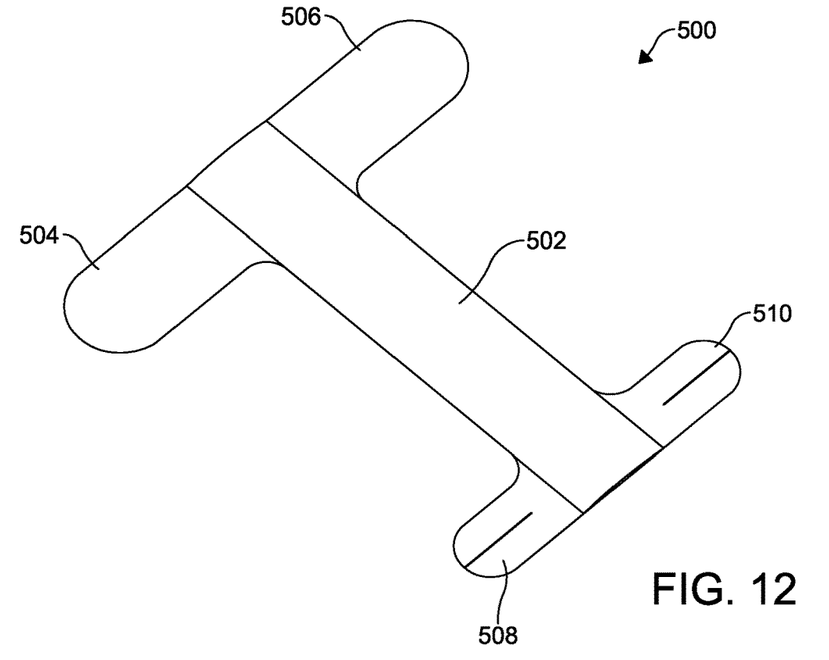
FIG. 12 shows an isometric view of a composite bandage according to embodiments of the disclosure.
Figure 13:
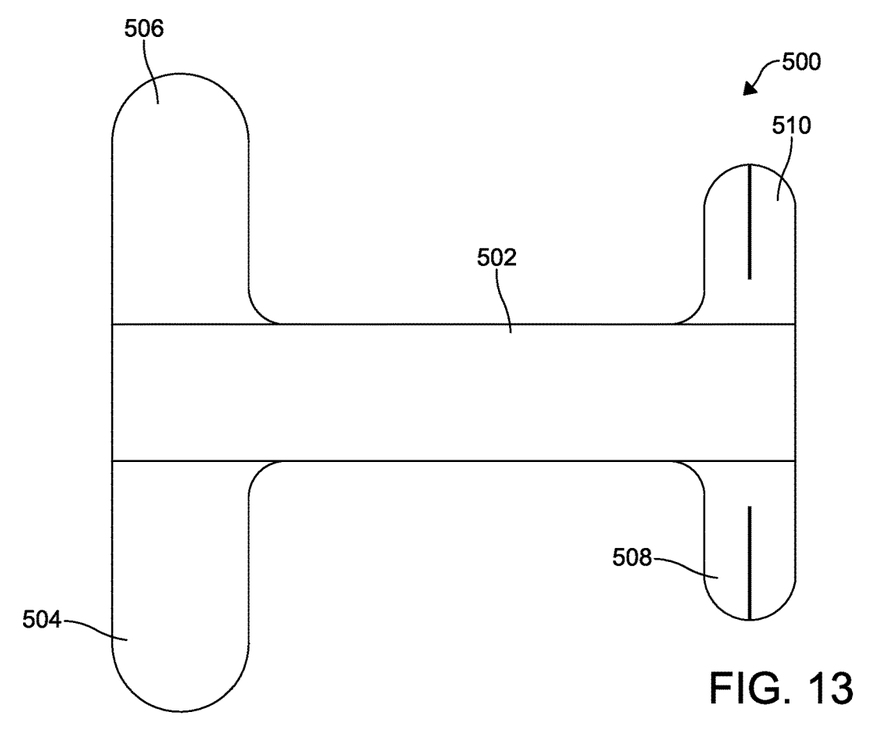
FIG. 13 shows a top view of a composite bandage according to embodiments of the disclosure.

In some embodiments, only the bunion support may be integrated with a footwear article (e.g., footwear article 300 of FIGS. 7-11). In one embodiment, footwear article 300 may be a sandal, as shown in FIGS. 7-11. FIG. 7 shows an isometric view of an example bunion support footwear article 300 according to embodiments of the disclosure. FIG. 8 shows the front view of example bunion support footwear article 300 according to embodiments of the disclosure. FIG. 9 shows a side view of example bunion support footwear article 300 according to embodiments of the disclosure. FIG. 10 shows a bottom view of example bunion support footwear article 300 according to embodiments of the disclosure. FIG. 11 shows a top view of example bunion support footwear article 300 according to embodiments of the disclosure.

The footwear article 300 may comprise a footbed 302 and an upper 304. The footbed 302 may further comprise a top surface 306 that would generally contact the bottom of a wearer's foot and a bottom surface 308 that would generally contact the ground. The upper 304 may comprise a y-shaped strap 310 having a first end that attaches to the footbed 302 in a first end 312 or region of the footwear article. The y-shaped strap 310 may be secured to the footbed 302 via any suitable means. The first end 312, when worn, may pass between the first and second toes of the wearer's foot. The strap 310 may also comprise first and second portions 314, 316 that extend laterally outward relative to the first end and attach to the footbed 302 near the footbed perimeter. When worn, the first and second strap portions 314, 316 wrap around portions of both sides of a foot. In the example shown, portions extend rearward as they extend laterally outward from first end 312 to overlie the foot rearward of the toes.

As with the support insole, the first end 312 of the footwear article upper 304 may comprise a bunion support (e.g., bunion support 204 of FIG. 6) which separates the big toe from the adjacent toe. As described herein, bunion support may be configured to keep maintain alignment of a first toe (e.g., the "big" toe) such that is relatively straighten, while maintaining separation between the first toe and the adjacent toe (e.g., the "pointer toe") when the footwear article is worn.

As can be seen in FIG. 10, footwear article footbed 302 may further comprise a textured bottom surface 308 to increase friction when worn. Textured bottom surface 308 may be formed in any pattern, using any of the methods of manufacturing described herein with respect to the support insole. Footwear article base or footbed may be ergonomically configured to provide additional support benefits for the wearer. Footwear article components may further be manufactured by any manufacturing process described herein. For cushioned support, footbed 302 may be constructed from a polymer or foam material, such as EVA.

In a further aspect of the disclosure, a composite bandage 400 is disclosed. FIG. 14 shows an isometric view of a composite bandage 400 according to embodiments of the disclosure. FIG. 15 shows a top view of a composite bandage 400 according to embodiments of the disclosure. The composite bandage 400 is configured to provide corrective positioning for a big toe of a wearer. The composite bandage 400 is formed using techniques similar to those used to form the support insole. In the instance of the composite bandage 400, a thin layer of carbon fiber may be inserted into a flexible polymer shell. As with other aspects of the invention, the composite bandage 400 may comprise a thin layer of carbon fiber inserted into a flexible shell. Particularly, the composite bandage 400 comprises a flexible main body 402 and a plurality of first and second tabs 404, 406, 408, 410 extending perpendicularly from first and second ends 412, 414 of the main body 402 and a support member disposed within at least the flexible main body to provide rigidity to the main body 402. The overall dimensions of the first tabs 404, 406 may be greater than the second tabs 408, 410. The ratio of the dimensions may be 2:1 or greater. Such a difference in dimension of the tabs may provide greater force for deformity correction in regions where it is needed, and provide greater comfort in other regions while also providing stability and adequate force to enable the correction. The first and second tabs 404, 406, 408, 410 may comprise rounded edges for further comfort. In some aspects, the composite bandage 400 may be disposable.

Methods for forming a composite bandage such as the composite bandage 400 may include one or more first fabrication processes. Fabrication processes for creating a composite bandage 400 may include extrusion, additive manufacturing (or 3D printing), and compression molding. For instance, the composite bandage 400 may be fabricated using a 3D PolyJet printer. Additive manufacturing or 3D printing allows for a fully supported print, enabling printing of flexible composite bandage 400 components. The materials used to form the composite bandage 400 may be selected based on desired material properties such as weight and elastic modulus. Elastomers (e.g., natural rubber, synthetic rubber, and thermoplastic elastomers) that provide sufficient elasticity and extensibility may be utilized or forming at least a portion of the flexible tabs or composite bandage sheath and/or other flexible components of the composite bandage 400. Advantageously, elastomers used to form the composite bandage flexible components may be soft to the touch and reduce or minimize skin irritation for a wearer, and provide a comfortable fit around the body that is resistant to tearing. In exemplary embodiments, a soft, flexible and tear resistant polymer, such as DuraForm® Flex is utilized. Other materials may be used, including, but not limited to, TangoBlack, TangoGray, or Agilus 30 FLX, and other DuraForm® polymers. Agilus30-FLX has high tensile tear resistance (5-7 kg-cm$^{-1}$). The Agilus30 family of polymers provides superior tear-resistance, elongation at break and rubber-like texture. In some embodiments, a fiber reinforced polymer (FRP) material may be used. A support resin (e.g., Fullcure 705) may be utilized during the printing process. In some aspects, composite bandage may be constructed using a 3D printed polymer such as a thermoplastic elastomer (TPU or TPE) which is soft, extensible and tear resistant. In some embodiments, composite bandage devices described herein may be a composite devices composed with metal or carbon fibers mixed with a polymer material, which may impart greater strength onto the composite bandage 400. For instance, a Connex 3D printer capable of printing with multi-material may be utilized to form composite bandage components.

The spine and foot supports described herein are designed to be flexible enough to be worn daily and provide correction over a period of time without the need for surgery while also providing comfort and functionality. The supports may also aid with inflammation and relieve pain during moments of discomfort. The supports may allow for wear of the device at any stage of a deformity to allow for the correction process to begin. The supports may also allow for simple manufacturing and changes to be made as the patients recovery progresses.

Various combinations of elements of this disclosure are encompassed by this disclosure, e.g., combinations of elements from dependent claims that depend upon the same independent claim.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

It is to be understood that the methods and systems are not limited to specific methods, specific components, or to particular implementations. It is also to be understood that the terminology used herein is for the purpose of describing particular embodiments only and is not intended to be limiting. Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the disclosure should be determined with reference to the appended claims, along with the full scope of equivalents to which such claims are entitled.

What is claimed is:

1. A support for a spine, the support comprising:
an elongate support body comprising a plurality of modular flexible support body segments extending along a longitudinal axis configured to align with one or more regions of a spinal column of a wearer;
a plurality of straps disposed along the longitudinal axis of the support body, wherein one or more of the plurality of straps is configured to releasably couple the support body to the wearer; and
a rigid support member disposed adjacent the support body and configured to provide rigidity to the support body, wherein the support body is disposed between the wearer and the support member when the support body is coupled to the wearer, wherein the support member acts as a cantilever configured to distribute a corrective force along the length of the support body, and wherein the support body segments are configured to rotate about the longitudinal axis of the support body independently of one another.

2. The support of claim 1, wherein the support body comprises a plurality of adjustment mechanisms configured to provide circumferential adjustment of the adjustable straps.

3. The support of claim 1, wherein the support body comprises a plurality of apertures configured to provide adjustment of the adjustable straps along the longitudinal axis of the support body.

4. The support of claim 1, wherein the support member is at least partially embedded in the support body.

5. The support of claim 1, wherein the support body is telescopic.

6. The support of claim 1, wherein the support body comprises a polymer.

7. The support of claim 1, wherein the support member comprises a metal.

8. The support of claim 1, wherein the support member comprises carbon fiber.

9. The support of claim 1, wherein the plurality of modular flexible support body segments comprises a first segment configured to align with a first area of a wearer.

10. The support of claim 9, wherein the first segment is configured to correspond with a neck area of a wearer.

11. The support of claim 9, wherein the plurality of modular flexible support body segments comprises a second segment configured to align with second area of wearer.

12. The support of claim 11, wherein the second segment is configured to correspond with an upper back or a mid-back area of a wearer.

13. The support of claim 11, wherein the second segment is configured to rotate independently from the first segment.

14. The support of claim 1, wherein the support body includes a plurality of segment apertures configured to receive on or more fasteners for affixing one or more support components to one or more of the plurality of modular flexible support body segments.

15. The support of claim 1, wherein at least one of the plurality of straps is configured to encircle a head region, a trunk region or a waist of a wearer.

16. The support of claim 1, wherein each of the plurality of straps comprises a strap fastener, further comprising one or more apertures configured to attached the strap fastener to a respective one of the plurality of modular flexible support body segments.

17. A support for a spine, the support comprising:
- an elongate support body comprising a plurality of telescoping support body segments extending along a longitudinal axis configured to align with one or more regions of a spinal column of a wearer;
- a plurality of straps disposed along the longitudinal axis of the support body, wherein one or more of the plurality of straps is configured to releasably couple the support body to the wearer; and
- a rigid support member disposed adjacent the support body, wherein the support body is disposed between the wearer and the support member when the support body is coupled to the wearer, and wherein the support member acts as a cantilever configured to distribute a corrective force along the length of the support body, and wherein the support body segments are configured to rotate about the longitudinal axis of the support body independently of one another.

\* \* \* \* \*